United States Patent [19]

Spietschka et al.

[11] Patent Number: 4,650,879
[45] Date of Patent: Mar. 17, 1987

[54] PROCESS FOR THE PREPARATION OF PERYLENE-3,4,9,10-TETRACARBOXYLIC DIANHYDRIDE

[75] Inventors: Ernst Spietschka, Idstein; Manfred Urban, Wiesbaden, both of Fed. Rep. of Germany

[73] Assignee: Hoechst Aktiengesellschaft, Fed. Rep. of Germany

[21] Appl. No.: 872,127

[22] Filed: Jun. 9, 1986

[30] Foreign Application Priority Data

Jun. 11, 1985 [DE] Fed. Rep. of Germany ....... 3520807

[51] Int. Cl.$^4$ .......................................... C07D 311/78
[52] U.S. Cl. .................................................... 549/232
[58] Field of Search .......................................... 549/232

[56] References Cited
FOREIGN PATENT DOCUMENTS
394794 9/1921 Fed. Rep. of Germany .

OTHER PUBLICATIONS
BIOS Final Report No. 1484, (4–14–54) p. 21.

Primary Examiner—Richard L. Raymond
Attorney, Agent, or Firm—Connolly and Hutz

[57] ABSTRACT

Process for the preparation of perylene-3,4,9,10-tetracarboxylic dianhydride of high purity and in a very good yield in an ecologically unobjectionable manner, which comprises saponifying perylene-3,4,9,10-tetracarboxylic acid diimide with a 2.5-fold to 6-fold amount by weight of 92.5% to 97.5% strength sulfuric acid at temperatures of 210° to 230° C., washing the resulting mixture of perylene-3,4,9,10-tetracarboxylic dianhydride and perylene-3,4,9,10-tetracarboxylic acid monoanhydride-monoimide with a 0-fold to 4-fold amount by weight of 80–95% strength sulfuric acid, and then washing it with water until it is neutral, converting the compounds present in the mixture into their potassium salts by means of potassium hydroxide, after removing the perylene-3,4,9,10-tetracarboxylic acid monoanhydride-monoimide, adding to the solution of the tetrapotassium salt of perylene-3,4,9,10-tetracarboxylic acid, under nitrogen and with the exclusion of air and light, a salt of iron, nickel, calcium, magnesium, aluminum, tin, copper, lead, zinc or manganese, suspended or dissolved in water, and allowing this salt to act at a pH>10 and at temperatures from 0° to 100° C., then clarifying the mixture and converting the tetrapotassium salt of perylene-3,4,9,10-tetracarboxylic acid by acidification into perylene-3,4,9,10-tetracarboxylic dianhydride and isolating the latter in a customary manner.

2 Claims, No Drawings

PROCESS FOR THE PREPARATION OF PERYLENE-3,4,9,10-TETRACARBOXYLIC DIANHYDRIDE

The invention relates to a process for the preparation of perylene-3,4,9,10-tetracarboxylic dianhydride of high purity and in a very good yield in an ecologically unobjectionable manner, starting from perylene-3,4,9,10-tetracarboxylic acid diimide.

Perylene-3,4,9,10-tetracarboxylic dianhydride is an important precursor for the preparation of pigments, vat dyestuffs and fluorescent dyestuffs. Stringent requirements are set in regard to its purity. The following processes are described in the literature for its preparation: in accordance with German Pat. No. 394,794 perylene-3,4,9,10-tetracarboxylic dianhydride is prepared by saponifying perylene-3,4,9,10-tetracarboxylic acid diimide in a 10-fold to 15-fold amount of concentrated sulfuric acid at about 200° C. According to BIOS Final Report No. 1484, page 21, perylene-3,4,9,10-tetracarboxylic acid diimide is saponified in a 10-fold amount of concentrated sulfuric acid at temperatures of 214°–216° C., and the crude perylene-3,4,10-tetracarboxylic dianhydride is filtered off and washed with a 10-fold amount of concentrated sulfuric acid. The crude perylene-3,4,9,10-tetracarboxylic dianhydride is dissolved in potassium hydroxide solution and separated off from perylene-3,4,9,10-tetracarboxylic acid diimide which has only been half-saponified (i.e. perylene-3,4,9,10-tetracarboxylic acid monoanhydride-monoimide). It is necessary to use large amounts of concentrated sulfuric acid in this process in order to remove colored by-products formed by oxidation and sulfonation processes, especially as the perylene-3,4,9,10-tetracarboxylic acid diimide employed is a technical grade having a purity <90%. As well as the poor space-time yield, the amounts of effluent containing sulfuric acid produced in these known processes constitute considerable technical problems. There was, therefore, a need for a process which permits pure perylene-3,4,9,10-tetracarboxylic dianhydride to be prepared by an ecologically unobjectionable route, without diminution in the yield or the purity required, but with a considerable minimization in the amount of sulfuric acid, particularly the amount of sulfuric acid used for washing. Admittedly a 2.5-fold to 6-fold amount of 95% strength sulfuric acid, relative to technical perylene-3,4,9,10-tetracarboxylic acid diimide, suffices for the saponification, at temperatures of 210°–230° C., of the perylene-3,4,9,10-tetracarboxylic acid diimide to the corresponding dianhydride, a lower limit being set for the amount of sulfuric acid by the stirring conditions of the equipment. However, even when washed vigorously with a 10-fold amount of concentrated sulfuric acid and worked up in accordance with the process of the state of the art, the crude perylene3,4,9,10-tetracarboxylic dianhydride obtained in this manner does not afford perylene-3,4,9,10-tetracarboxylic dianhydride satisfying the requirements in respect of purity.

It has now been found that perylene-3,4,9,10-tetracarboxylic dianhydride of high purity can be prepared in a very good yield and in an ecologically unobjectionable manner by saponifying perylene-3,4,9,10-tetracarboxylic acid diimide with a 2.5-fold to 6-fold amount by weight of 92.5 to 97.5% strength sulfuric acid, preferably a 3-fold to 5-fold amount by weight of 95% strength sulfuric acid, at temperatures of 210° to 230° C., preferably 215° to 220° C., washing the resulting mixture of perylene-3,4,9,10-tetracarboxylic dianhydride and perylene-3,4,9,10-tetracarboxylic acid diimide which has only been half-saponified (i.e. perylene-3,4,9,10-tetracarboxylic acid monoanhydride-monoimide) with a 0-fold to 4-fold amount by weight of 80–95% strength sulfuric acid, preferably 80% strength sulfuric acid, and then washing the mixture with water until it is neutral, then converting the two said compounds present in the mixture into their potassium salts by means of potassium hydroxide, after removing the perylene-3,4,9,10-tetracarboxylic acid monoanhydride-monoimide, adding to the solution of the tetrapotassium salt of perylene-3,4,9,10-tetracarboxylic acid, under nitrogen and with the exclusion of air and light, a salt of iron, nickel, calcium, magnesium, aluminum, tin, copper, lead, zinc or manganese, suspended or dissolved in water, and allowing this salt to act at a pH > 10 and at temperatures from 0° to 100° C., then clarifying the mixture and converting the tetrapotassium salt of perylene-3,4,9,10-tetracarboxylic acid by acidification into perylene-3,4,9,10-tetracarboxylic dianhydride and isolating the latter in a customary manner, i.e. by filtering it off, washing it with water until it is neutral and drying it.

The perylene-3,4,9,10-tetracarboxylic dianhydride thus obtained meets all the requirements in respect of purity and yield. The nature of the anions of the salts of the metals indicated above depends on their availability. Essentially, they are chlorides, sulfates and carbonates. The metal salts mentioned are expediently added in an amount of 25% to 200%, preferably in an amount of about 50%, relative to the weight of the tetrapotassium salt of perylene-3,4,9,10-tetracarboxylic acid. The best purifying effects are achieved if about 50% is added, taking account, where appropriate, of water of crystallization and molecular weight. It is also advantageous to add active charcoal. It was surprising that, in this procedure, only the impurities are precipitated, in the form of their salts, and not the sparingly soluble salts of perylene-3,4,9,10-tetracarboxylic dianhydride with the cations of the metals mentioned. The clarification sludge produced in this clarification is also added to the sulfuric acid filtrate from the crude perylene-3,4,9,10-tetracarboxylic dianhydride after it has been diluted to <20% strength, and the precipitated residue is removed. Not only does this measure effect decolorization of the red-colored effluent, but, at the same time, toxic compounds interfering with biodegradation are removed. The purifying effect and the improvement in the effluent can, of course, also be achieved if the process is carried out at a greater dilution of the sulfuric acid.

The examples below are intended to illustrate the process according to the invention, without limiting it thereto.

EXAMPLE 1

800 g of 95% strength sulfuric acid are initially taken and 200 g of 89.4% strength perylene-3,4,9,10-tetracarboxylic acid diimide are introduced at room temperature. The temperature of the mixture is then raised to 220° C. and is maintained at this level for two hours. The mixture is then allowed to cool to room temperature and the precipitate which has been formed is filtered off with suction and washed with water until it is neutral. 174.3 g of crude perylene-3,4,9,10-tetracarboxylic dianhydride are obtained after drying at 80° C. This is introduced, with exclusion of light, into a solution composed of 6 liters of water and 140 g of 85% strength potassium hydroxide. While blanketed with nitrogen, the solution is heated to 80°–90° C., and stirring is continued for a further 90 minutes at this temperature. The solution is then allowed to cool to 25° C., the pH is adjusted to a value of 8–9 and the solid residue is filtered off with suction and washed with 100 ml of water. (The residue is 38.8 g of perylene-3,4,9,10-tetracarboxylic acid diimide which has only been half-saponified, i.e. perylene-3,4,9,10-tetracarboxylic acid monoanhydride-monoimide, and this is expediently added to the next batch.) 60 g of 85% strength potassium hydroxide and 60 g of animal charcoal are introduced into the filtrate, with the exclusion of light, and the solution is then blanketed with nitrogen. After a further hour's stirring at 25° C., a solution of 60 g of iron(II) sulfate and 600 ml of water is added dropwise, the mixture is stirred for a further hour at 25° C. and is clarified and the filtrate is then added dropwise to 600 g of concentrated hydrochloric acid, the mixture is kept at 80°–90° C. for one hour and the precipitate is filtered off with suction, washed with water until it is neutral and dried at 80° C. 120.9 g of perylene-3,4,9,10-tetracarboxylic dianhydride are obtained.

The purity of the perylene-3,4,9,10-tetracarboxylic dianhydride is determined by the following method:

(a) Dissolving the sample:

2.5 g of perylene-3,4,9,10-tetracarboxylic dianhydride are introduced into 40 ml of water. After 1.75 g of 85% strength potassium hydroxide have been added, the mixture is stirred, under nitrogen and with exclusion of air, for 30 minutes at 50° C., whereupon solution takes place. The solution is then filtered through a folded filter into a vessel flushed with nitrogen. The resulting solution is kept in the dark until the determination is carried out.

(b) Determination:

Measurements are carried out by means of the DU 7 spectral photometer (made by Beckmann), using a 1-cm cell. The base line of the solution mixture is recorded without weighing the sample. The absorption spectra are recorded between 800 nm and 500 nm.

(c) Results:

Readings of the extinction values measured against extinction at 780 nm are taken at 580 nm and 570 nm. The perylene-3,4,9,10-tetracarboxylic dianhydride obtained in accordance with Example 1 gives the following extinction values: 1.43 at 580 nm; 2.50 at 570 nm.

If the clarification residue composed of animal charcoal and iron(II) sulfate is added to the sulfuric acid filtrate which has been diluted with water, clarification gives an effluent which is not toxic to fish, not toxic to bacteria and excellently biodegradable, having a degradation ratio of 81.4%. Without this measure, the degradation ratio is only 8% and, in addition, the toxicity to bacteria is retained.

EXAMPLE 2

800 g of 95% strength sulfuric acid are initially taken and 200 g of 89.4% strength perylene-3,4,9,10-tetracarboxylic acid diimide are introduced at room temperature. The temperature of the mixture is then raised to 220° C., and this temperature is maintained for two hours. The mixture is then allowed to cool to room temperature and the precipitate which has been formed is filtered off with suction and washed first with 280 g of 80% strength sulfuric acid and then with water until it is neutral. Drying at 80° C. gives 171.6 g of crude perylene-3,4,9,10-tetracarboxylic dianhydride. This is introduced, with exclusion of light, into a solution composed of six liters of water and 140 g of 85% strength potassium hydroxide. While blanketed with nitrogen, the solution is heated to 80°–90° C., and stirring is continued for a further 90 minutes at this temperature. The mixture is then allowed to cool to 25° C., the pH is adjusted to a value of 8–9 and the solid residue is filtered off with suction and washed with 100 ml of water. (The residue is 34.1 g of perylene-3,4,9,10-tetracarboxylic acid diimide which has only been half-saponified, i.e. perylene-3,4,9,10-tetracarboxylic acid monoanhydride-monoimide, and this is expediently added to the next batch.) 60 g of 85% strength potassium hydroxide and 60 g of animal charcoal are introduced into the filtrate, with exclusion of light, and the mixture is then blanketed with nitrogen. After a further hour's stirring at 25° C., a solution of 60 g of iron(II) sulfate and 600 ml of water is added dropwise, the mixture is stirred for a further hour at 25° C. and is clarified, and the filtrate is then added dropwise to 600 g of concentrated hydrochloric acid, the mixture is kept at 80°–90° C. for one hour and the precipitate is filtered off with suction, washed with water until it is neutral and dried at 80° C. This gives 125.1 g of perylene-3,4,9,10-tetracarboxylic dianhydride having the following extinction values:

0.76 at 580 nm and
1.39 at 570 nm (The purity is determined by the method indicated in Example 1).

EXAMPLE 3

800 g of 95% strength sulfuric acid are initially taken and 200 g of 89.4% strength perylene-3,4,9,10-tetracarboxylic acid diimide are introduced at room temperature. The temperature of the mixture is then raised to 220° C. and maintained at this level for two hours. The mixture is then allowed to cool to room temperature and the precipitate which has been formed is filtered off with suction and washed first with 280 g of 80% strength sulfuric acid and then with water until it is neutral. Drying at 80° C. gives 170.9 g of crude perylene-3,4,9,10-tetracarboxylic dianhydride. This is introduced, with exclusion of light, into a solution composed of six liters of water and 140 g of 85% strength potassium hydroxide. While blanketed with nitrogen, the solution is heated to 80°–90° C. and stirring is continued for a further 90 minutes at this temperature. The mixture is then allowed to cool to 25° C., the pH is adjusted to a value of 8–9 and the solid residue is filtered off and washed with 100 ml of water. (The residue is 35.6 g of perylene-3,4,9,10-tetracarboxylic acid diimide which has been only half-saponified, i.e. perylene-3,4,9,10-tetracarboxylic acid monoanhydride-monoimide, and this is expediently added to the next batch.) 120 g of 85% strength potassium hydroxide are introduced into the filtrate, with exclusion of light, and the mixture is then blanketed with nitrogen. After a further hour's stirring at 25° C., a solution of 120 g of iron(II) sulfate and 600 ml of water is added dropwise, the mixture is stirred for a further hour at 25° C. and clarified and the filtrate is then added dropwise to 600 g of concentrated hydrochloric acid, the mixture is kept at 80°–90° C. for one hour and the precipitate is filtered off, washed with water until it is neutral and dried at 80° C. This gives 130.8 g of perylene-3,4,9,10-tetracarboxylic dianhydride having the following extinction values:

0.84 at 580 nm and 1.46 at 570 nm.
(The purity is determined by the method indicated in Example 1.)

EXAMPLE 4

800 g of 95% strength sulfuric acid are initially taken and 200 g of 89.4% strength perylene-3,4,9,10-tetracarboxylic acid diimide are introduced at room temperature. The temperature of the mixture is then raised to 220° C., and this temperature is maintained for two hours. The mixture is then allowed to cool to room temperature and the precipitate which has been formed is filtered off with suction and washed first with 280 g of 80% strength sulfuric acid and then with water until it is neutral. Drying at 80° C. gives 170.9 g of crude perylene-3,4,9,10-tetracarboxylic dianhydride. This is introduced, with exclusion of light, into a solution composed of six liters of water and 140 g of 85% strength potassium hydroxide. While blanketed with nitrogen, the solution is heated to 80°-90° C., and stirring is continued for a further 90 minutes at this temperature. The mixture is then allowed to cool to 25° C., the pH is adjusted to a value of 8-9 and the solid residue is filtered off with suction and washed with 100 ml of water. (The residue is 35.6 g of perylene-3,4,9,10-tetracarboxylic acid diimide which has only been half-saponified, i.e. perylene-3,4,9,10-tetracarboxylic acid monoanhydride-monoimide, and this is expediently added to the next batch.) 60 g of 85% strength potassium hydroxide and 60 g of animal charcoal are introduced into the filtrate, with exclusion of light, and the mixture is then blanketed with nitrogen. After a further hour's stirring at 25° C., a solution of 110 g of nickel(II) sulfate crystals in 600 ml of water is added dropwise, the mixture is stirred for a further hour at 25° C. and is clarified, and the filtrate is then added dropwise to 600 g of concentrated hydrochloric acid, the mixture is kept at 80°-90° C. for one hour and the precipitate is filtered off with suction, washed with water until it is neutral and dried at 80° C. This gives 121.8 g of perylene-3,4,9,10-tetracarboxylic dianhydride having the following extinction values:
0.80 at 580 nm and
1.42 at 570 nm.
(The purity is determined by the method indicated in Example 1.)

EXAMPLE 5

800 g of 95% strength sulfuric acid are initially taken and 200 g of 89.4% strength perylene-3,4,9,10-tetracarboxylic acid diimide are introduced at room temperature. The temperature of the mixture is then raised to 220° C., and this temperature is maintained for two hours. The mixture is then allowed to cool to room temperature and the precipitate which has been formed is filtered off with suction and washed first with 280 g of 80% strength sulfuric acid and then with water until it is neutral. Drying at 80° C. gives 172.1 g of crude perylene-3,4,9,10-tetracarboxylic dianhydride. This is introduced, with exclusion of light, into a solution composed of six liters of water and 140 g of 85% strength potassium hydroxide. While blanketed with nitrogen, the solution is heated to 80°-90° C., and stirring is continued for a further 90 minutes at this temperature. The mixture is then allowed to cool to 25° C., the pH is adjusted to a value of 8-9 and the solid residue is filtered off with suction and washed with 100 ml of water. (The residue is 33.3 g of perylene-3,4,9,10-tetracarboxylic acid diimide which has only been half-saponified, i.e. perylene-3,4,9,10-tetracarboxylic acid monoanhydride-monoimide, and this is expediently added to the next batch.) 60 g of 85% strength potassium hydroxide and 60 g of animal charcoal are introduced into the filtrate, with exclusion of light, and the mixture is then blanketed with nitrogen. After a further hour's stirring at 25° C., a solution of 263 g of aluminum sulfate crystals in 600 ml of water is added dropwise, the mixture is stirred for a further hour at 25° C. and is clarified, and the filtrate is then added dropwise to 600 g of concentrated hydrochloric acid, the mixture is kept at 80°-90° C. for one hour and the precipitate is filtered off with suction, washed with water until it is neutral and dried at 80° C. This gives 119.6 g of perylene-3,4,9,10-tetracarboxylic dianhydride having the following extinction values:
0.69 at 580 nm and
1.29 at 570 nm.
(The purity is determined by the method indicated in Example 1.)

EXAMPLE 6

800 g of 95% strength sulfuric acid are initially taken and 200 g of 89.4% strength perylene-3,4,9,10-tetracarboxylic acid diimide are introduced at room temperature. The temperature of the mixture is then raised to 220° C., and this temperature is maintained for two hours. The mixture is then allowed to cool to room temperature and the precipitate which has been formed is filtered off with suction and washed first with 280 g of 80% strength sulfuric acid and then with water until it is neutral. Drying at 80° C. gives 170.9 g of crude perylene-3,4,9,10-tetracarboxylic dianhydride. This is introduced, with exclusion of light, into a solution composed of six liters of water and 140 g of 85% strength potassium hydroxide. While blanketed with nitrogen, the solution is heated to 80°-90° C., and stirring is continued for a further 90 minutes at this temperature. The mixture is then allowed to cool to 25° C., the pH is adjusted to a value of 8-9 and the solid residue is filtered off with suction and washed with 100 ml of water. (The residue is 36.1 g of perylene-3,4,9,10-tetracarboxylic acid diimide which has only been half-saponified, i.e. perylene-3,4,9,10-tetracarboxylic acid monoanhydride-monoimide, and this is expediently added to the next batch.) 60 g of 85% strength potassium hydroxide and 60 g of animal charcoal are introduced into the filtrate, with exclusion of light, and the mixture is then blanketed with nitrogen. After a further hour's stirring at 25° C., a solution of 84 g of magnesium chloride crystals in 600 ml of water is added dropwise, the mixture is stirred for a further hour at 25° C. and is clarified, and the filtrate is then added dropwise to 600 g of concentrated hydrochloric acid, the mixture is kept at 80°-90° C. for one hour and the precipitate is filtered off with suction, washed with water until it is neutral and dried at 80° C. This gives 126.1 g of perylene-3,4,9,10-tetracarboxylic dianhydride having the following extinction values:
0.82 at 580 nm and
1.44 at 570 nm.
(The purity is determined by the method indicated in Example 1.)

EXAMPLE 7

800 g of 95% strength sulfuric acid are initially taken and 200 g of 89.4% strength perylene-3,4,9,10-tetracarboxylic acid diimide are introduced at room temperature. The temperature of the mixture is then raised to 220° C., and this temperature is maintained for two hours. The mixture is then allowed to cool to room temperature and the precipitate which has been formed is filtered off with suction and washed first with 280 g of 80% strength sulfuric acid and then with water until it is neutral. Drying at 80° C. gives 172.3 g of crude perylene-3,4,9,10-tetracarboxylic dianhydride. This is introduced, with exclusion of light, into a solution composed of six liters of water and 140 g of 85% strength potassium hydroxide. While blanketed with nitrogen, the solution is heated to 80°–90° C., and stirring is continued for a further 90 minutes at this temperature. The mixture is then allowed to cool to 25° C., the pH is adjusted to a value of 8–9 and the solid residue is filtered off with suction and washed with 100 ml of water. (The residue is 34.3 g of perylene-3,4,9,10-tetracarboxylic acid diimide which has only been half-saponified, i.e. perylene-3,4,9,10-tetracarboxylic acid monoanhydride-monoimide, and this is expediently added to the next batch.) 60 g of 85% strength potassium hydroxide and 60 g of animal charcoal are introduced into the filtrate, with exclusion of light, and the mixture is then blanketed with nitrogen. After a further hour's stirring at 25° C., a solution of 111.6 g of calcium chloride crystals in 600 ml of water is added dropwise, the mixture is stirred for a further hour at 25° C. and is clarified, and the filtrate is then added dropwise to 600 g of concentrated hydrochloric acid, the mixture is kept at 80°–90° C. for one hour and the precipitate is filtered off with suction, washed with water until it is neutral and dried at 80° C. This gives 121.2 g of perylene-3,4,9,10-tetracarboxylic dianhydride having the following extinction values:

0.65 at 580 nm and
1.26 at 570 nm.

(The purity is determined by the method indicated in Example 1.)

EXAMPLE 8

800 g of 95% strength sulfuric acid are initially taken and 200 g of 89.4% strength perylene-3,4,9,10-tetracarboxylic acid diimide are introduced at room temperature. The temperature of the mixture is then raised to 220° C., and this temperature is maintained for two hours. The mixture is then allowed to cool to room temperature and the precipitate which has been formed is filtered off with suction and washed first with 280 g of 80% strength sulfuric acid and then with water until it is neutral. Drying at 80° C. gives 172.4 g of crude perylene-3,4,9,10-tetracarboxylic dianhydride. This is introduced, with exclusion of light, into a solution composed of six liters of water and 140 g of 85% strength potassium hydroxide. While blanketed with nitrogen, the solution is heated to 80°–90° C., and stirring is continued for a further 90 minutes at this temperature. The mixture is then allowed to cool to 25° C., the pH is adjusted to a value of 8–9 and the solid residue is filtered off with suction and washed with 100 ml of water. (The residue is 35.0 g of perylene-3,4,9,10-tetracarboxylic acid diimide which has only been half-saponified, i.e. perylene-3,4,9,10-tetracarboxylic acid monoanhydride-monoimide, and this is expediently added to the next batch.) 60 g of 85% strength potassium hydroxide and 60 g of animal charcoal are introduced into the filtrate, with exclusion of light, and the mixture is then blanketed with nitrogen. After a further hour's stirring at 25° C., a solution of 60 g of iron(III) chloride and 600 ml of water is added dropwise, the mixture is stirred for a further hour at 25° C. and is clarified, and the filtrate is then added dropwise to 600 g of concentrated hydrochloric acid, the mixture is kept at 80°–90° C. for one hour and the precipitate is filtered off with suction, washed with water until it is neutral and dried at 80° C. This gives 125.6 g of perylene-3,4,9,10-tetracarboxylic dianhydride having the following extinction values:

0.77 at 580 nm and
1.43 at 570 nm.

(The purity is determined by the method indicated in Example 1.)

EXAMPLE 9

800 g of 95% strength sulfuric acid are initially taken and 200 g of 89.4% strength perylene-3,4,9,10-tetracarboxylic acid diimide are introduced at room temperature. The temperature of the mixture is then raised to 220° C., and this temperature is maintained for two hours. The mixture is then allowed to cool to room temperature and the precipitate which has been formed is filtered off with suction and washed first with 280 g of 80% strength sulfuric acid and then with water until it is neutral. Drying at 80° C. gives 174.3 g of crude perylene-3,4,9,10-tetracarboxylic dianhydride. This is introduced, with exclusion of light, into a solution composed of six liters of water and 140 g of 85% strength potassium hydroxide. While blanketed with nitrogen, the solution is heated to 80°–90° C., and stirring is continued for a further 90 minutes at this temperature. The mixture is then allowed to cool to 25° C., the pH is adjusted to a value of 8–9 and the solid residue is filtered off with suction and washed with 100 ml of water. (The residue is 38.7 g of perylene-3,4,9,10-tetracarboxylic acid diimide which has only been half-saponified, i.e. perylene-3,4,9,10-tetracarboxylic acid monoanhydride-monoimide, and this is expediently added to the next batch.) 60 g of 85% strength potassium hydroxide and 60 g of animal charcoal are introduced into the filtrate, with exclusion of light, and the mixture is then blanketed with nitrogen. After a further hour's stirring at 25° C., a solution of 48.8 g of copper carbonate and 600 ml of water is added dropwise, the mixture is stirred for a further hour at 25° C. and is clarified, and the filtrate is then added dropwise to 600 g of concentrated hydrochloric acid, the mixture is kept at 80°–90° C. for one hour and the precipitate is filtered off with suction, washed with water until it is neutral and dried at 80° C. This gives 133.7 g of perylene-3,4,9,10-tetracarboxylic dianhydride having the following extinction values:

0.99 at 580 nm and
1.54 at 570 nm.

(The purity is determined by the method indicated in Example 1.)

We claim:

1. A process for the preparation of perylene-3,4,9,10-tetracarboxylic dianhydride of high purity and in a very good yield and in an ecologically unobjectionable manner, which comprises saponifying perylene-3,4,9,10-tetracarboxylic acid diimide with a 2.5-fold to 6-fold amount by weight of 92.5 to 97.5% strength sulfuric acid at temperatures of 210° to 230° C., washing the resulting mixture of perylene-3,4,9,10-tetracarboxylic dianhydride and perylene-3,4,9,10-tetracarboxylic acid monoanhydride-monoimide with a 0-fold to 4-fold amount by weight of 80–95% strength sulfuric acid, and then washing it with water until it is neutral, converting the two mentioned compounds present in the mixture into their potassium salts by means of potassium hydroxide, after removing the perylene-3,4,9,10-tetracarboxylic acid monoanhydride-monoimide, adding to the solution of the tetrapotassium salt of perylene-3,4,9,10-tetracarboxylic acid, under nitrogen and with the exclusion of air and light, a salt of iron, nickel, calcium, magnesium, aluminum, tin, copper, lead, zinc or manganese, suspended or dissolved in water, and allowing it to act at a pH > 10 and at temperatures from 0° to 100° C., and then clarifying the mixture and converting the tetrapotassium salt of perylene-3,4,9,10-tetracarboxylic acid by acidification into perylene-3,4,9,10-tetracarboxylic dianhydride and isolating the latter in a customary manner.

2. The process as claimed in claim 1, wherein aqueous solutions or suspensions of the chlorides, sulfates or carbonates of iron, nickel, calcium, magnesium, aluminum, tin, copper, lead, zinc or manganese are added.

* * * * *